United States Patent [19]

Bonnery et al.

[11] Patent Number: 5,405,994
[45] Date of Patent: Apr. 11, 1995

[54] DISODIUM 4-CHLOROPHENYLTHIOMETHYLENEBIS-PHOSPHONATE MONOHYDRATE, ITS PREPARATION AND PHARMACEUTICAL COMPOSITIONS IN WHICH IT IS PRESENT

[75] Inventors: Michel Bonnery, Vailhauques; Michel Bouisset; Raphaël Sole, both of Sisteron, all of France

[73] Assignee: Sanofi, Paris, France

[21] Appl. No.: 101,742

[22] Filed: Aug. 4, 1993

[30] Foreign Application Priority Data

Aug. 5, 1992 [FR] France ................. 92 09718

[51] Int. Cl.[6] ............................ A61K 31/66
[52] U.S. Cl. ............................ 562/21
[58] Field of Search ........................ 562/21

[56] References Cited

U.S. PATENT DOCUMENTS 4,746,654  5/1988  Breliere et al. ............... 514/108
4,876,248 10/1989  Breliere et al. ............... 514/108
4,922,007  5/1990  Kieczykowski et al. ......... 562/13

OTHER PUBLICATIONS

Bonnery et al, Bull. Soc. Chim. (1), 1988, pp. 49–56.
Barbier et al. Agents and Actions v. 16 (1–2) 1985 pp. 41–42.
Bonnery et al; Bulletin de la Societe Chimique de France; No. 1; 1988; pp. 49–56.

*Primary Examiner*—José G. Dees
*Assistant Examiner*—Joseph M. Conrad
*Attorney, Agent, or Firm*—Bacon & Thomas

[57] ABSTRACT

The present invention relates to disodium 4-chlorophenylmethylenebisphosphonate monohydrate. The invention also relates to a method of preparing this form of the monohydrate, as well as to pharmaceutical compositions in which disodium tiludronate monohydrate is present as the active principle.

12 Claims, 10 Drawing Sheets

DISODIUM 4-CHLOROPHENYLTHIOMETHYLENEBIS-PHOSPHONATE MONOHYDRATE, ITS PREPARATION AND PHARMACEUTICAL COMPOSITIONS IN WHICH IT IS PRESENT

The present invention relates to disodium 4-chlorophenylthiomethylenebisphosphonate monohydrate.

The invention further relates to the method of preparing this monohydrate.

It is known in the literature that some bisphosphonic acids and their salts are capable of forming hydrates.

Thus hydrates of 1-hydroxyethylidenebisphosphonic acid (International Non-proprietary Name: etidronic acid) and of its sodium salts are described in Zh. Obshch. Khim., 1987, 57(3), 538–544.

The crystalline form of dimethylaminomethylenebisphosphonic acid monohydrate is described in Kristallografiya, 1990, 35(6), 1442–9.

Monosodium 4-amino-1-hydroxybutylidenebisphosphonate is described in the form of the trihydrate in J. Pharm. Biochem. Anal., 1989, 7(12), 1719–1727.

U.S. Pat. No. 4,711,880 and European patent 177 443 describe the crystalline pentahydrate form of the disodium salt of 3-amino-1-hydroxypropylidenebisphosphonic acid (International Non-proprietary Name: pamidronic acid) and its method of preparation.

European patent 100 718 describes methylenebisphosphonic acid derivatives of the formula $$\begin{array}{c} R_1O \\ \diagdown \\ R_1O \end{array} \!\! \overset{O}{\underset{\|}{P}} \!\!-\!\! \overset{R_3}{\underset{|}{C}} \!\!-\!\! \overset{O}{\underset{\|}{P}} \!\! \begin{array}{c} OR_1 \\ \diagup \\ OR_1 \end{array}$$
$$\begin{array}{c} | \\ (CH_2)_n \\ | \\ S \\ | \\ R_2 \end{array}$$
(I)

in which:

$R_1$ is hydrogen or a linear or branched lower alkyl group having from 1 to 4 carbon atoms;

$R_2$ is:
hydrogen,
an alkyl group which is unsubstituted or substituted by a hydroxyl or thiol group or one or more halogen atoms, an alkoxycarbonyl group or a group $$-N\diagup^{Z_1}_{\diagdown Z_2}$$

in which $Z_1$ and $Z_2$, taken independently, are hydrogen or a lower alkyl group, a phenyl group which is unsubstituted or monosubstituted or polysubstituted by a halogen, a nitro group, a lower alkyl, lower alkoxy or trifluoromethyl group or else an $NH_2$ group or a COOH or COOalkyl group, a group $$-\overset{X}{\underset{\|}{C}}-N\diagup^{Z_1}_{\diagdown Z_2}$$

in which X is oxygen or sulfur and $Z_1$ and $Z_2$ are as defined above, a 5- or 6-membered heterocycle containing 1 or 2 heteroatoms selected from nitrogen and sulfur, or a 5-membered heterocycle fused with a benzene ring and having the formula

[structure with X and $R_4$ substituents on fused bicyclic ring]

in which X can be oxygen, an NH group or sulfur and $R_4$ is hydrogen or a halogen atom, preferably chlorine;

$R_3$ denotes hydrogen; and n is an integer between 0 and 10, with the proviso that:

$R_2$ is other than a methyl or pyridyl group when $R_1$=H and n=0, $R_2$ is other than the group of the formula

[phenyl ring with $OCH_3$ and Q substituents]

in which Q is a halogen atom, a nitro group or a trifluoromethyl group, when $R_1$ is the methyl or ethyl group and n=0, $R_2$ is other than the phenyl group when $R_1$ is the ethyl group and n=0, and $R_2$ is not an unsubstituted alkyl or phenyl group or an acetoxy group when n=1, and the salts of said derivatives in which $R_1$=H with mineral and organic bases.

Said patent also describes the method of preparing the compounds of formula (I).

These compounds are esters when $R_1$ is a lower alkyl or acids when $R_1$ is hydrogen. According to the procedure described, the compounds (I) in which $R_1$ is hydrogen are prepared by acid hydrolysis from the compounds of formula (I) in which $R_1$ is an alkyl. The reaction is carried out by refluxing the ester in dilute hydrochloric acid. After isolation by evaporation, the acid thus obtained can be converted to one of its salts in known manner.

Example 9 of European patent 100 718 describes the preparation of 4-chlorophenylthiomethylenebisphosphonic acid and its ditert-butylamine salt.

European patent 336 851 describes pharmaceutical compositions for oral administration which are based on a bisphosphonic acid derivative, in particular 4-chlorophenylthiomethylenebisphosphonic acid or its disodium salt, and contain from 1.5% to 6% by weight of sodium laurylsulfate.

4-Chlorophenylthiomethylenebisphosphonic acid has been given the non-proprietary name "tiludronic acid" and the disodium salt is of this tiludronic acid, also called sodium tiludronate, has been chosen for development as a drug which is useful in the treatment of rheumatoid polyarthritis, Paget's disease or osteoporosis.

The physicochemical analysis of this salt, prepared by the method described in European patent 100 718, has now shown that it is disodium tiludronate hemihydrate and not disodium tiludronate monohydrate as could have been implied from its elemental analysis. Indeed, said elemental analysis, as indicated in Bull. Soc. Chim. Fr., 1988, No.1, pages 49–55, shows that the salt crystallizes with one molecule of water. However, the physicochemical analysis shows that said molecule of water consists, in effect, in half a molecule of hydration and half a molecule of impregnation; thereby proving that the prior art salt is a hemihydrate.

It has now been found, totally surprisingly, that a novel crystalline form of disodium tiludronate exists. This crystalline form is disodium tiludronate monohydrate and is a subject of the present invention.

The analysis of this crystalline form has shown that it differs from the previously known form of sodium tiludronate by its physicochemical characteristics.

Thus, according to a further subject of the present invention, disodium tiludronate monohydrate is characterized by its IR spectrum, its X-ray spectrum, its weight loss curve on thermogravimetric analysis, and its DCA spectrum, which has an endothermic peak at $121° \pm 8°$ C.

The method of preparing the disodium tiludronate monohydrate is a further subject of the present invention. This method comprises heating disodium tiludronate hemihydrate in aqueous solution at a temperature of between 60° C. and 90° C. for a period of between 2 hours and 24 hours, leaving it to cool to a temperature of between room temperature and 5° C., filtering off the precipitate formed and then drying it.

In one particular embodiment, disodium tiludronate hemihydrate can be prepared in situ from an aqueous solution of tiludronic acid by the addition of a sufficient amount of sodium hydroxide to bring the pH to between 4.6 and 4.8.

The disodium tiludronate hemihydrate in aqueous solution can be heated in the presence of a water-miscible solvent selected from the group consisting of acetone, ethanol and isopropyl alcohol.

The dilution of the disodium tiludronate hemihydrate in the aqueous solution can vary in a ratio of 1 part by weight of salt to 2 to 10 parts by volume of water.

When a water-miscible solvent is used, its volume can vary in a ratio of 1 to 25 relative to the weight of the disodium tiludronate and, independently, in a ratio of 0.5 to 2.5 relative to the volume of water.

In one variant of the method, the disodium tiludronate hemihydrate in crystalline form, distributed as a thin layer, is treated in the presence of water in a closed chamber heated to between 65° C. and 75° C., for 1 to 5 days, and then dried.

The compound formed can be dried in a ventilated oven at a temperature of between 50° C. and 70° C. The drying can also be completed by azeotropic distillation in the presence of an appropriate solvent. Examples which may be mentioned of solvents useful for azeotropic distillation are isopropyl ether, ethyl acetate, 3-methylbutanone, n-butanol, dichloroethane or toluene.

Disodium tiludronate monohydrate is particularly stable with time, irrespective of the humidity and temperature conditions.

The monohydrate can be used to prepare pharmaceutical compositions, forming subjects of the present invention, which are also particularly stable.

The pharmaceutical compositions according to the present invention include especially tablets for oral administration.

The pharmaceutical compositions according to the present invention can also contain ingredients normally used in pharmacy, for example a disintegrating agent, a flow control agent or any suitable bulk excipient.

Bulk excipients which can be used are lactose, cellulose or starches. Lubricants which can be used are stearic acid, magnesium stearate, L-leucine or, for example, glycerol tribehenate. Disintegrating agents which can be used are sodium carboxymethyl starch, crosslinked sodium carboxymethyl cellulose or, for example, crosslinked polyvinylpyrrolidone. Flow control agents which can be used are pure silica or colloidal silicon dioxide.

The present invention further relates to instantaneously dissolving oral forms and to effervescent oral forms obtained by adding an effervescent couple to the composition according to the invention. Examples of effervescent couples which can be used are tartaric acid and sodium bicarbonate or citric acid and sodium bicarbonate.

The tablet form is a preferred form according to the invention. The invention further relates to instantaneously dissolving tablets, effervescent tablets and coated tablets.

In the remainder of the description, by way of convenience, disodium tiludronate hemihydrate, as known previously, is referred to as form 1 and disodium tiludronate monohydrate, a subject of the present invention, is referred to as form 2.

The following abbreviations are also used:

RT: room temperature
l: liter
DCA: differential calorimetric analysis

Forms 1 and 2 of disodium tiludronate obtained below have a melting point above 250° C.

A) Preparation of 4-chlorophenylthiomethylenebisphosphonic acid

Tetraisopropyl 4-chlorophenylthiomethylenebisphosphonate is prepared by applying the method described in European patent 100 718. This compound is treated with water and hydrochloric acid and heated at 90° C. for several hours. After cooling, extraction is carried out with dichloroethane. The aqueous phase is concentrated under vacuum to remove the hydrochloric acid and the water. Toluene is added and the residual water is driven off by distillation. 4-Chlorophenylthiomethylenebisphosphonic acid precipitates on cooling. This precipitate is collected by filtration, washed with toluene and dried at a temperature less than or equal to 70° C.

B) Preparation of disodium 4-chlorophenylthiomethylenebisphosphonate (form 1)

Sodium hydroxide, either as pellets or as an aqueous solution, is added to an aqueous suspension of the acid obtained above until the pH is about 4.7. Active charcoal is added and the mixture is clarified by filtration.

The filtrate is mixed with acetone and the expected salt precipitates at RT.

The precipitate is collected by filtration, washed with acetone and dried at a temperature less than or equal to 70° C.

Starting from the aqueous solution at pH 4.7, it is also possible to precipitate the salt by the addition of ethanol followed by cooling of the medium to 10° C.

Various physicochemical methods are used to analyze and characterize the salt obtained in this way.

Figure 1:
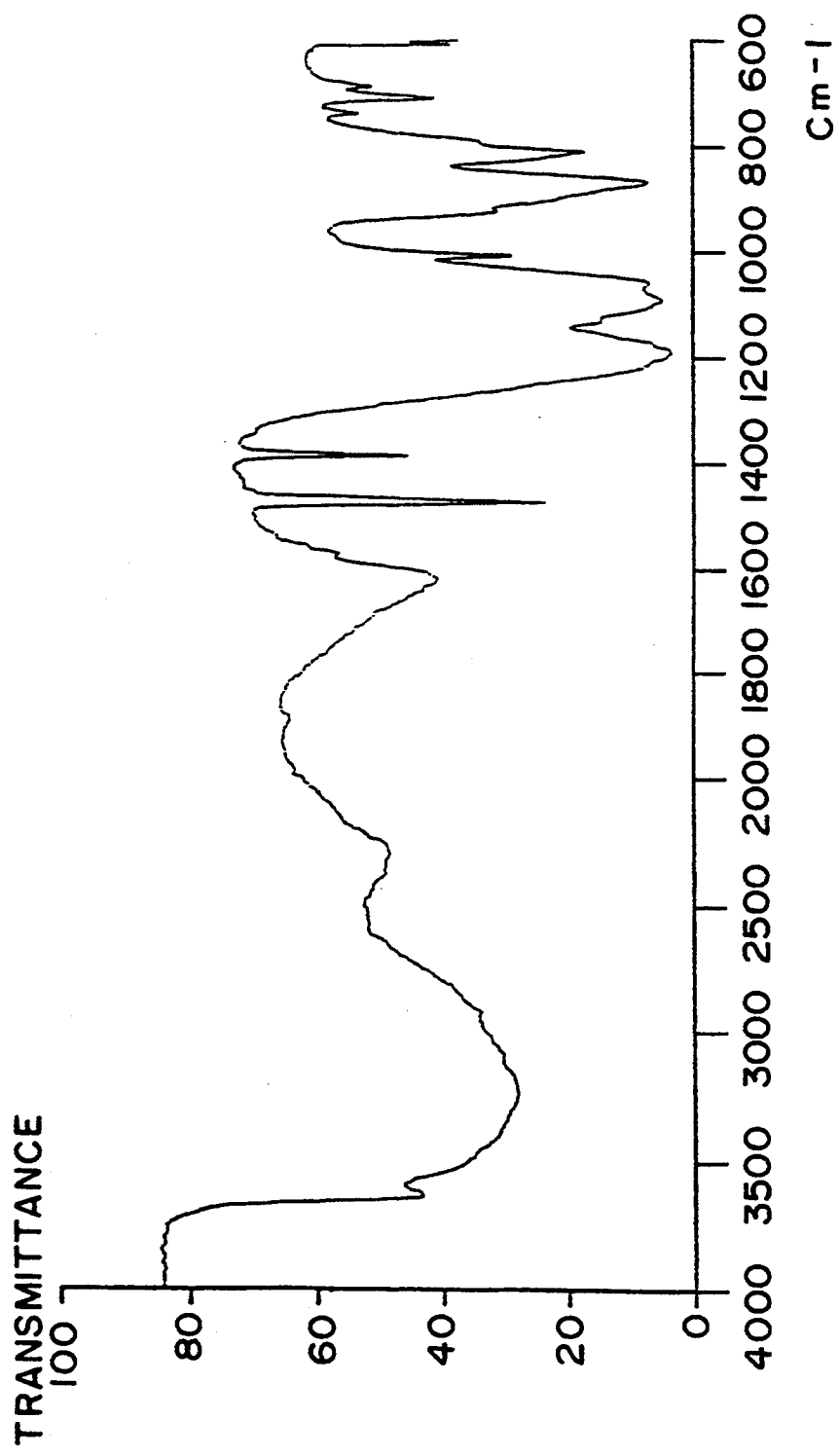
FIGS. 1–10 display several of the physical characteristic which define the instant compound.

IR Run at 1% (m/v) in Potassium Bromide: FIG. 1

| | |
|---|---|
| 1600 cm$^{-1}$ and 1480 cm$^{-1}$: | C-C aromatic |
| 1390 cm$^{-1}$: | C-H |
| 1090 cm$^{-1}$ and 1050 cm$^{-1}$: | P-O |
| 820 cm$^{-1}$: | C-H |
| 710 cm$^{-1}$: | C-S |

Figure 2:
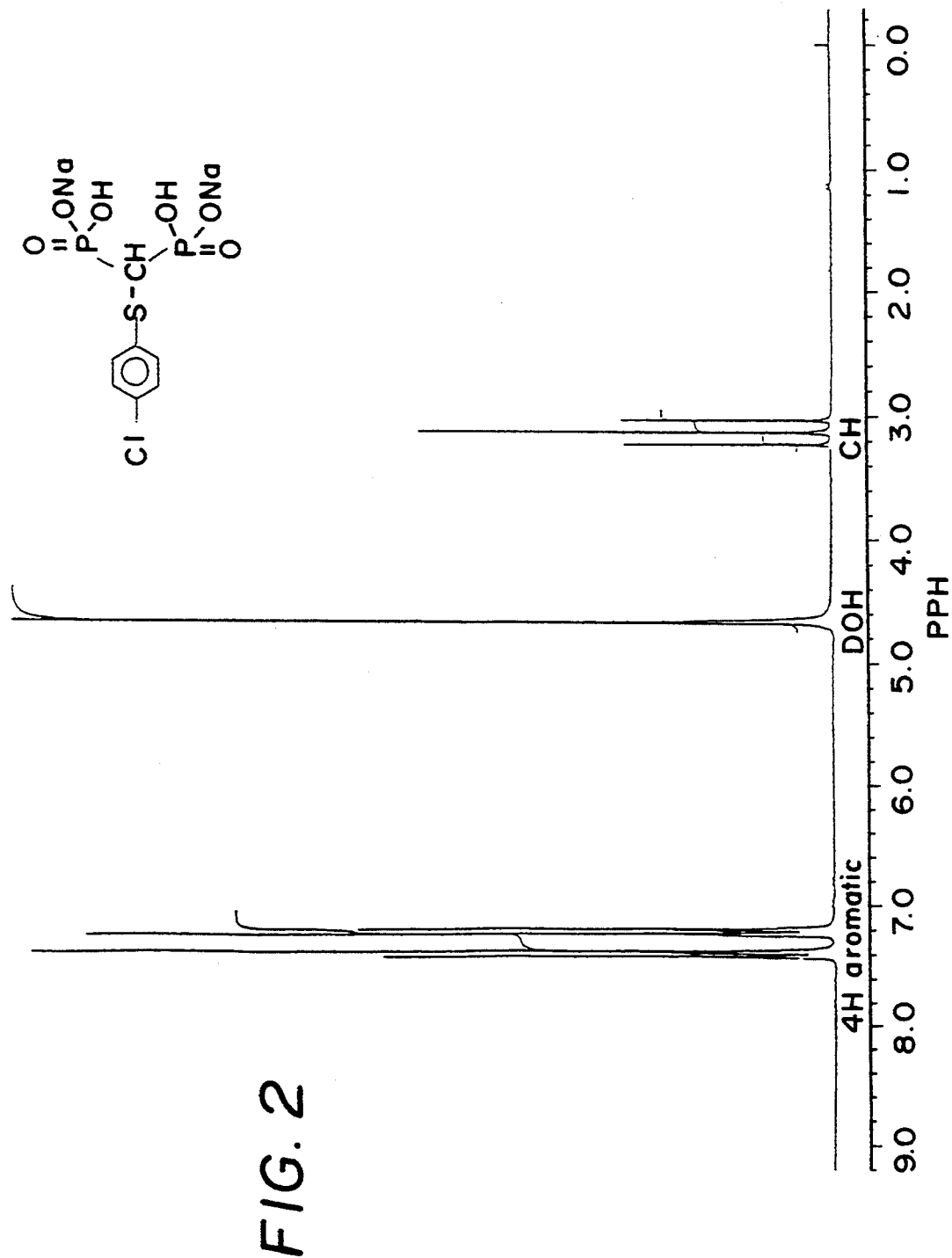

NMR Run at 250 MHz in D$_2$O: FIG. 2

Elemental analysis: $C_7H_5ClO_6P_2SNa_2$; water content: 4.9%; theoretical C:23.19, H:1.95, S:8.84, Cl:9.78; measured C:21.65, H:2.26, S:8.54, Cl:9.18; corrected C:22.76, H:1.80, S:8.98, Cl:9.65.

The "corrected" value is obtained from the "measured" value by allowing for the water content.

The water content indicates the presence of the equivalent of one molecule of water per molecule of product, corresponding to half a molecule of hydration and half a molecule of impregnation, as indicated below.

Figure 3:
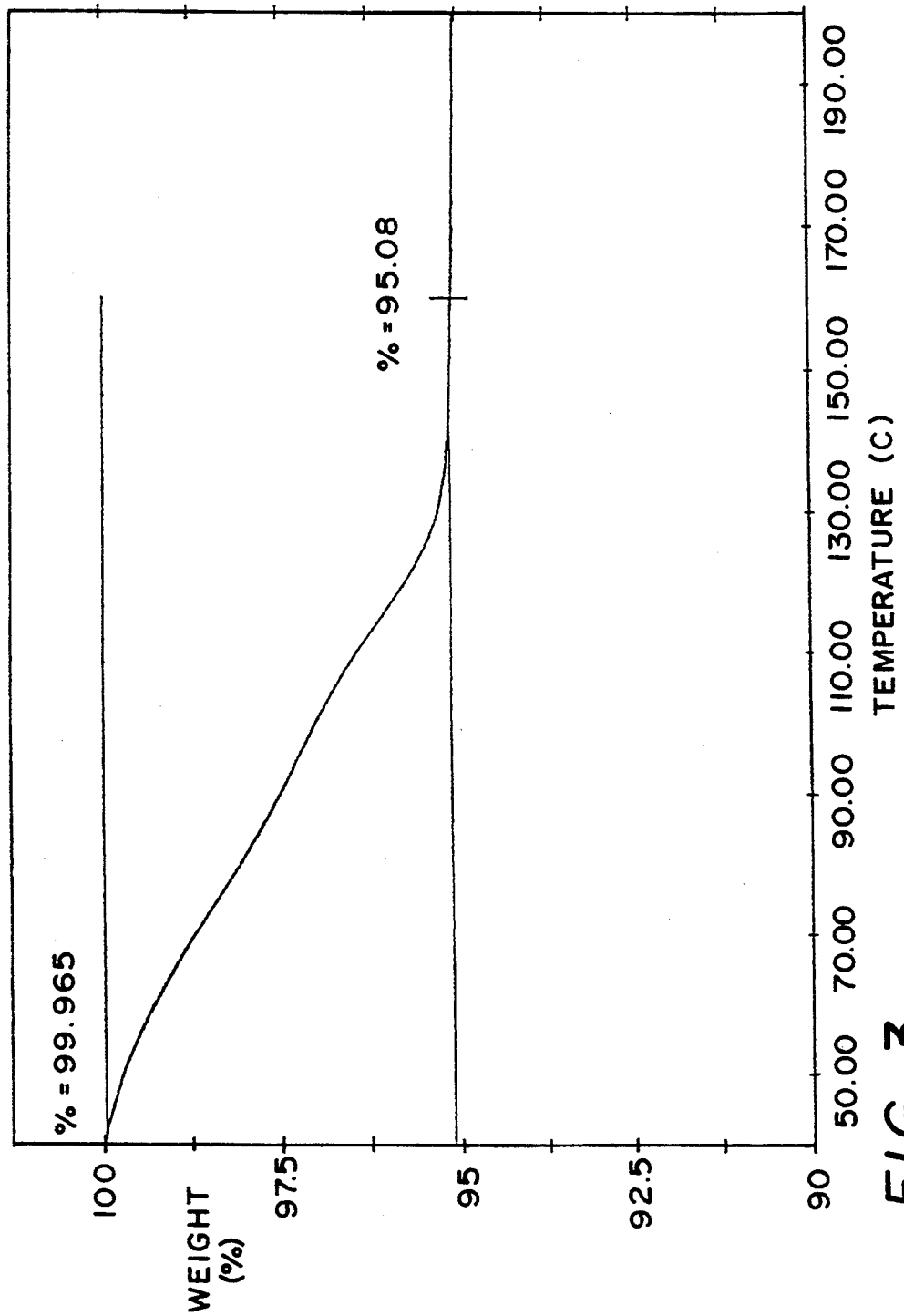

Weight Loss Curve on Thermogravimetric Analysis: FIG. 3

The thermogravimetric analysis is performed on a Perkin-Elmer TGA 7 apparatus equipped with a data processing terminal. The system is calibrated against the Curie points of alumel and nickel. The heating rate is 10.0° C. per minute and the temperature range is 40° C. to 200° C. The purging gas for the balance is nitrogen. The sample weight is 5.160 mg.

FIG. 3 shows that the curve indicates two successive weight losses:
- between 40° C. and 90° C., the loss of 0.5 mol of water of impregnation is observed,
- between 90° C. and 160° C., the loss of 0.5 mol of water of hydration is observed.

It can be deduced from this that form 1 is disodium tiludronate hemihydrate, which comprises about half a molecule of additional water corresponding to the half-molecule of impregnation.

Figure 4:
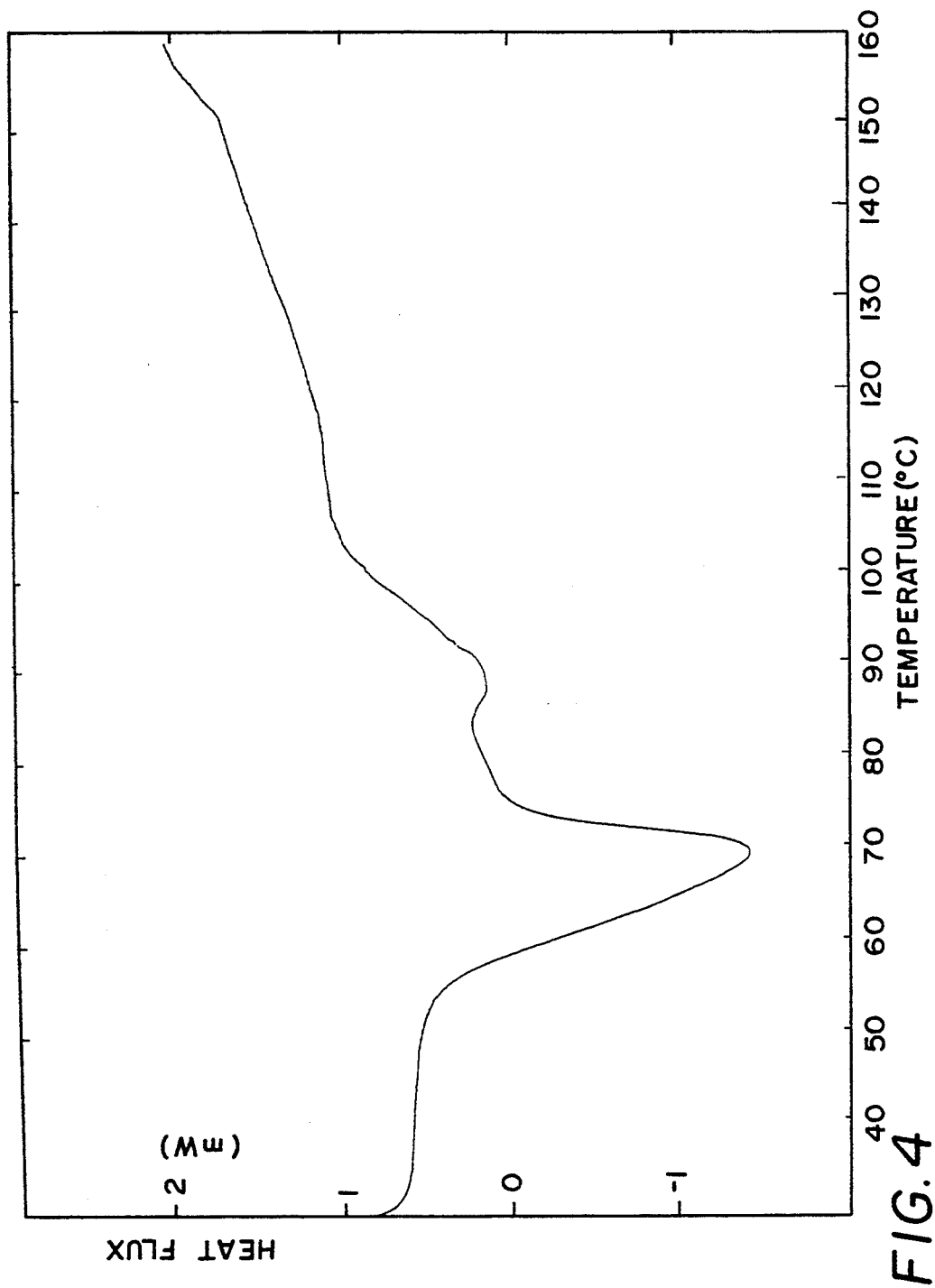

Differential Calorimetric Analysis: FIG. 4

This analysis is performed on a Setaram DSC 101 apparatus sold by Setaram, Lyon, France. The initial temperature is 20° C. and rises to 150° C. at a rate of 1.0° C. per minute. The sample weight is 10 mg.

Figure 5:
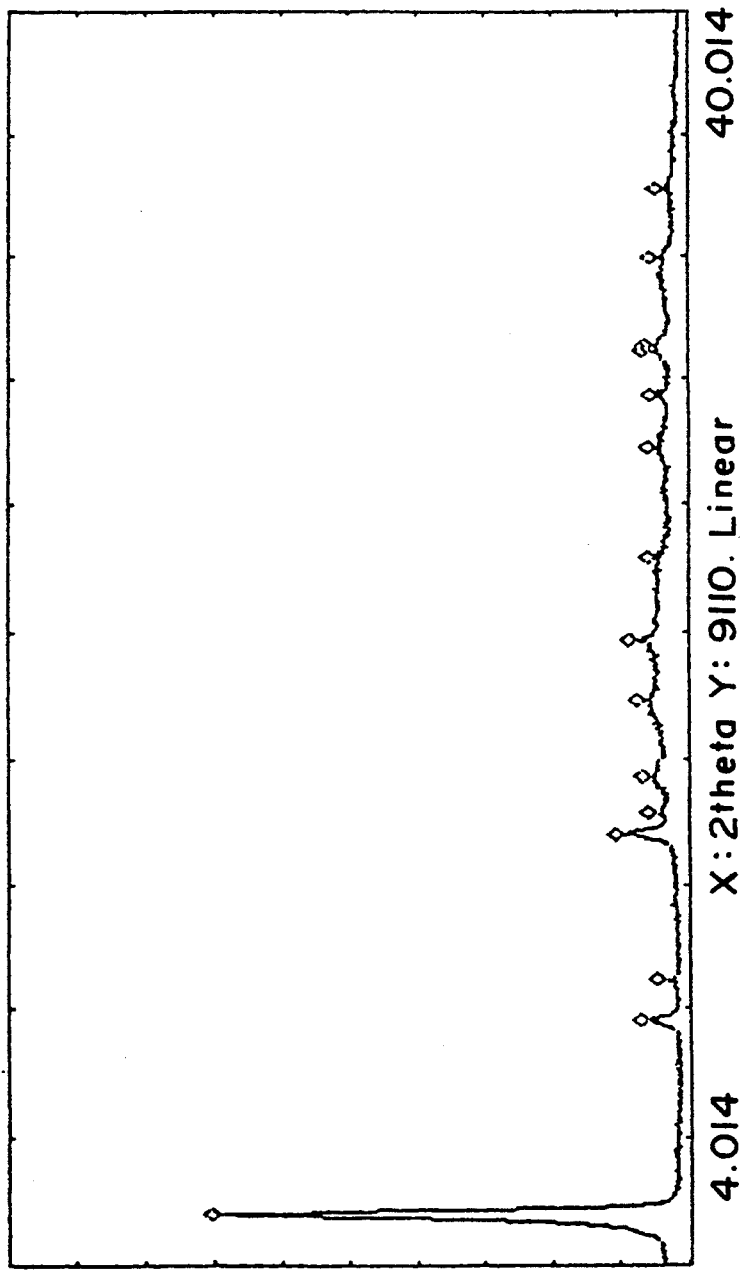

X-Ray Diffraction Spectrum: FIG. 5

The powder diagram is produced on a Siemens D 500 TT diffractometer of the theta-theta type, equipped with a copper anode, for 2theta values of between 4° and 40°.

The spectrum has a principal line at 5.4 and less intense lines at 16.3, 21.8 and 20.1, as indicated in Table 1 below.

TABLE 1

| 2theta | d | I rel. | 2theta | d | I rel. |
|---|---|---|---|---|---|
| 5.408 | 16.3281 | 100.0 | 5.408 | 16.3281 | 100.0 |
| 10.841 | 8.1546 | 8.2 | 16.306 | 5.4317 | 13.1 |
| 12.011 | 7.3626 | 4.4 | 21.806 | 4.0725 | 10.4 |
| 16.306 | 5.4317 | 13.1 | 20.110 | 4.4121 | 8.9 |
| 16.877 | 5.2491 | 6.4 | 10.841 | 8.1546 | 8.2 |
| 17.910 | 4.9485 | 7.7 | 17.910 | 4.9485 | 7.7 |
| 20.110 | 4.4121 | 8.9 | 30.067 | 2.9697 | 7.4 |
| 21.806 | 4.0725 | 10.4 | 30.230 | 2.9541 | 7.0 |
| 24.144 | 3.6832 | 6.6 | 24.144 | 3.6832 | 6.6 |
| 27.242 | 3.2710 | 6.5 | 27.242 | 3.2710 | 6.5 |
| 28.760 | 3.1017 | 6.0 | 16.877 | 5.2491 | 6.4 |
| 30.067 | 2.9697 | 7.4 | 32.837 | 2.7253 | 6.0 |
| 30.230 | 2.9541 | 7.0 | 28.760 | 3.1017 | 6.0 |
| 32.837 | 2.7253 | 6.0 | 12.011 | 7.3626 | 4.4 |
| 34.928 | 2.5668 | 4.4 | 34.928 | 2.5668 | 4.4 |

The following Examples describe the preparation of disodium tiludronate monohydrate (form 2) by applying the method according to the invention.

EXAMPLE 1

An aqueous solution of disodium tiludronate (form 1) is prepared by mixing 100 g of the salt with 1 liter of water and this solution is clarified by filtration. 2.3 liters of acetone are brought to the reflux point and the above aqueous solution is poured in, reflux being maintained for 3 hours. The medium is left to return to room temperature and is then cooled for 1 hour at 10° C. The precipitate formed is filtered off and then dried overnight at 60° C. in a ventilated oven to give 95 g of the expected product in the form of crystals.

Figure 6:
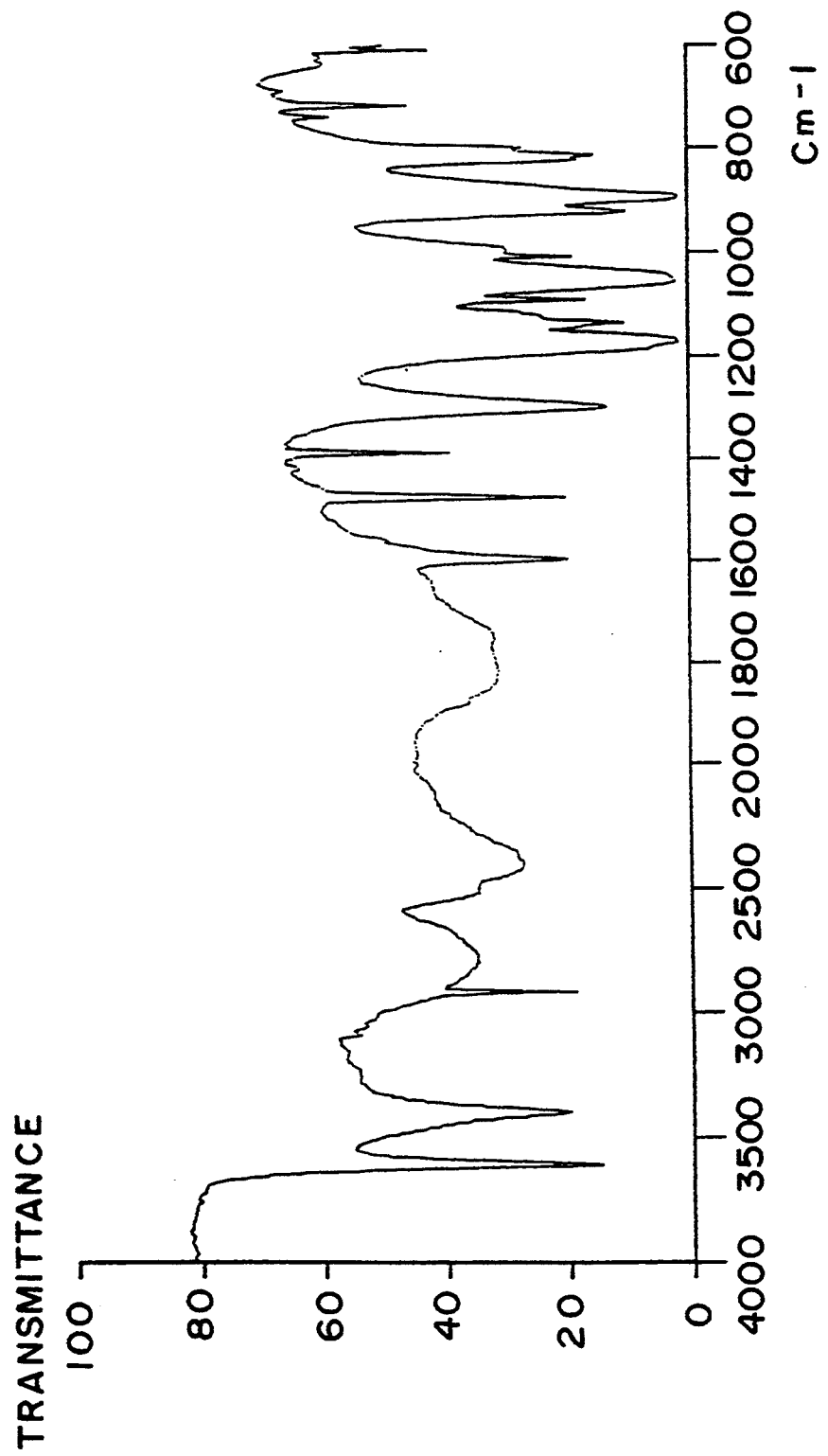

IR Run at 1% (m/v) in Potassium Bromide: FIG. 6

Some bands are the same as those observed with form 1 and others are different.

| | |
|---|---|
| 1600 cm$^{-1}$ and 1480 cm$^{-1}$: | C-C aromatic |
| 1390 cm$^{-1}$: | C-H |
| 1090 cm$^{-1}$ and 1050 cm$^{-1}$: | P-0 |
| 820 cm$^{-1}$: | C-H |
| 710 cm$^{-1}$: | C-S |
| new bands: | |
| 3600 cm$^{-1}$ | |
| 3400 cm$^{-1}$ | |
| 2920 cm$^{-1}$ | |
| 1300 cm$^{-1}$ | |
| 900 cm$^{-1}$ | |

Figure 7:
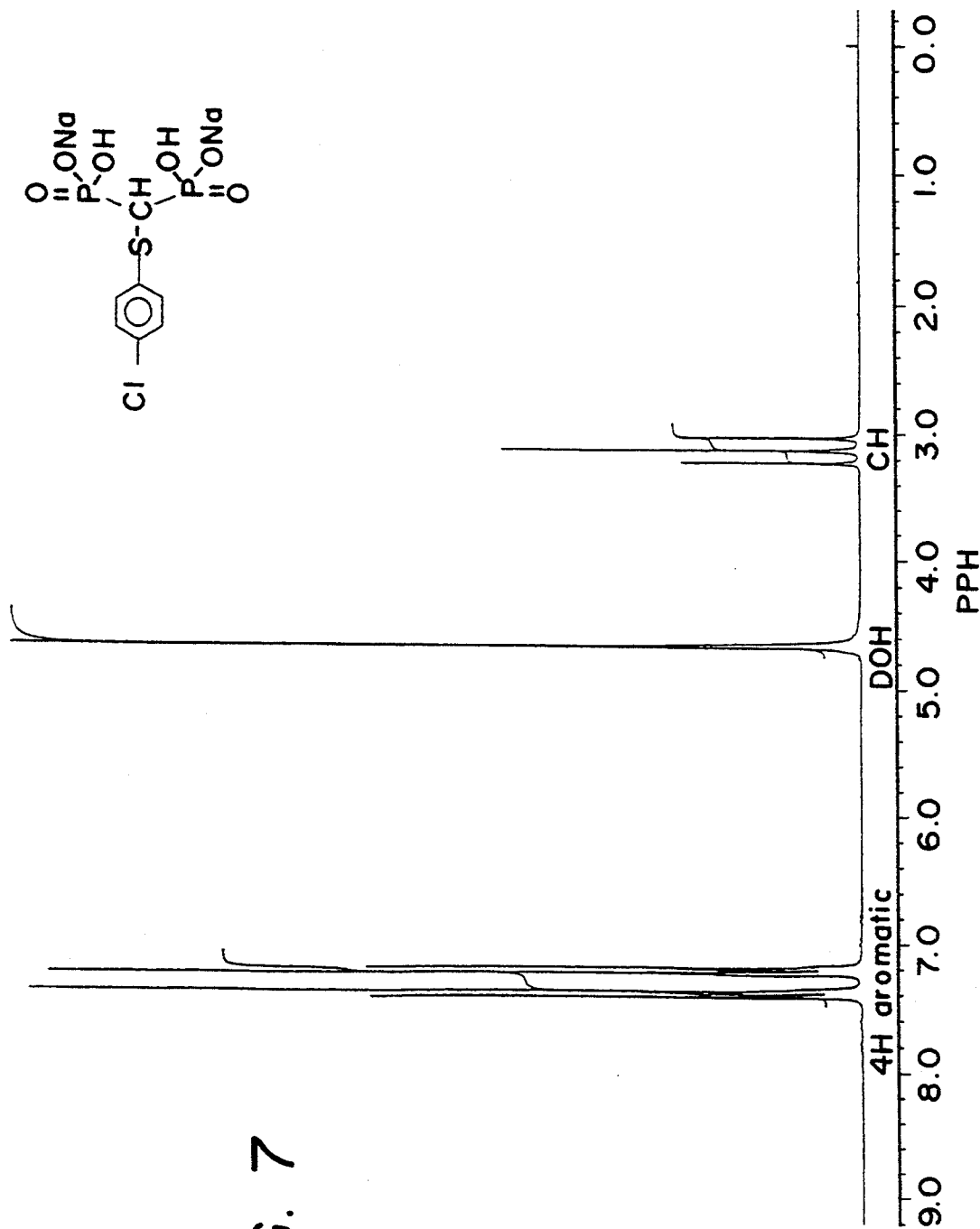

The NMR spectrum (FIG. 7) is identical to that run with form 1 under the same conditions.

Elemental analysis: $C_7H_5ClO_6P_2SNa_2.H_2O$; theoretical C:22.09, H:2.38, S:8.42, Cl:9.31, H$_2$O:4.72; found C:21.99, H:2.54, S:8.40, Cl:9.80, H$_2$O:4.77.

Figure 8:
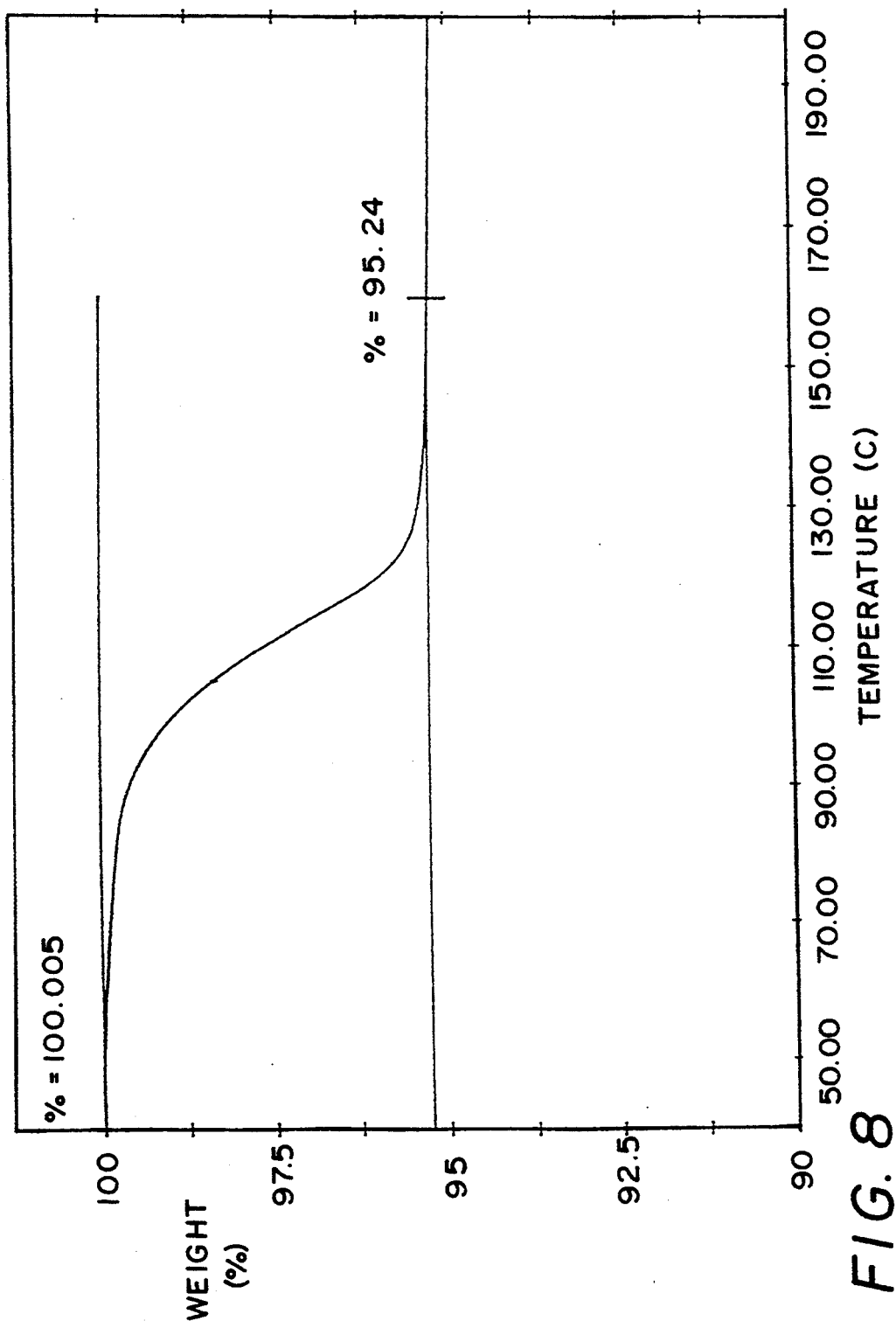

Weight Loss Curve on Thermogravimetric Analysis: FIG. 8

The sample weight is 5.178 mg. The operating conditions are identical to those indicated for form 1.

The curve shows a weight loss between 90° C. and 160° C. which corresponds to the loss of one mol of water of hydration.

Figure 9:
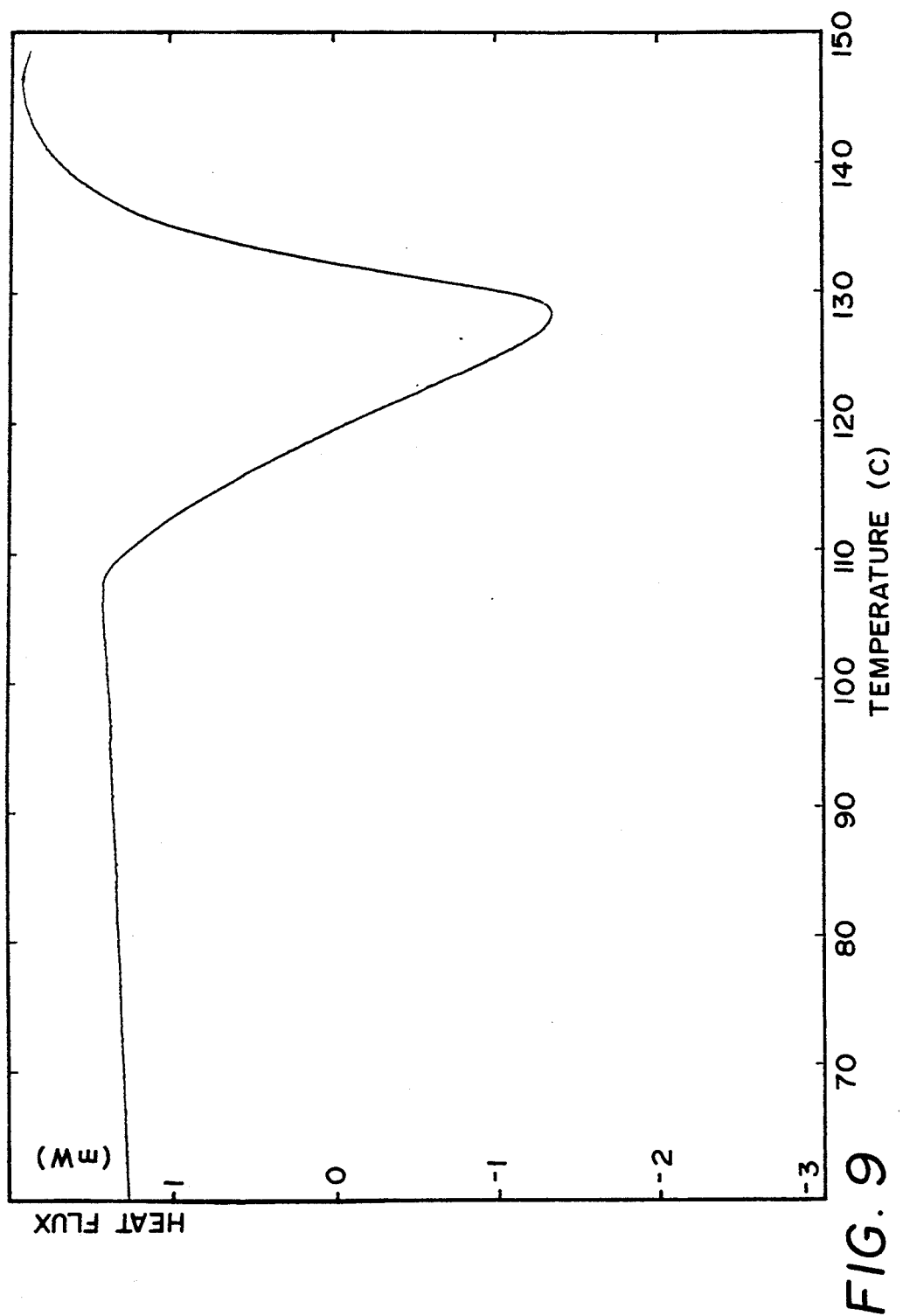

Differential Calorimetric Analysis: FIG. 9

The conditions are those described for form 1.

An endothermic peak centred at 129° C. is observed.

Figure 10:
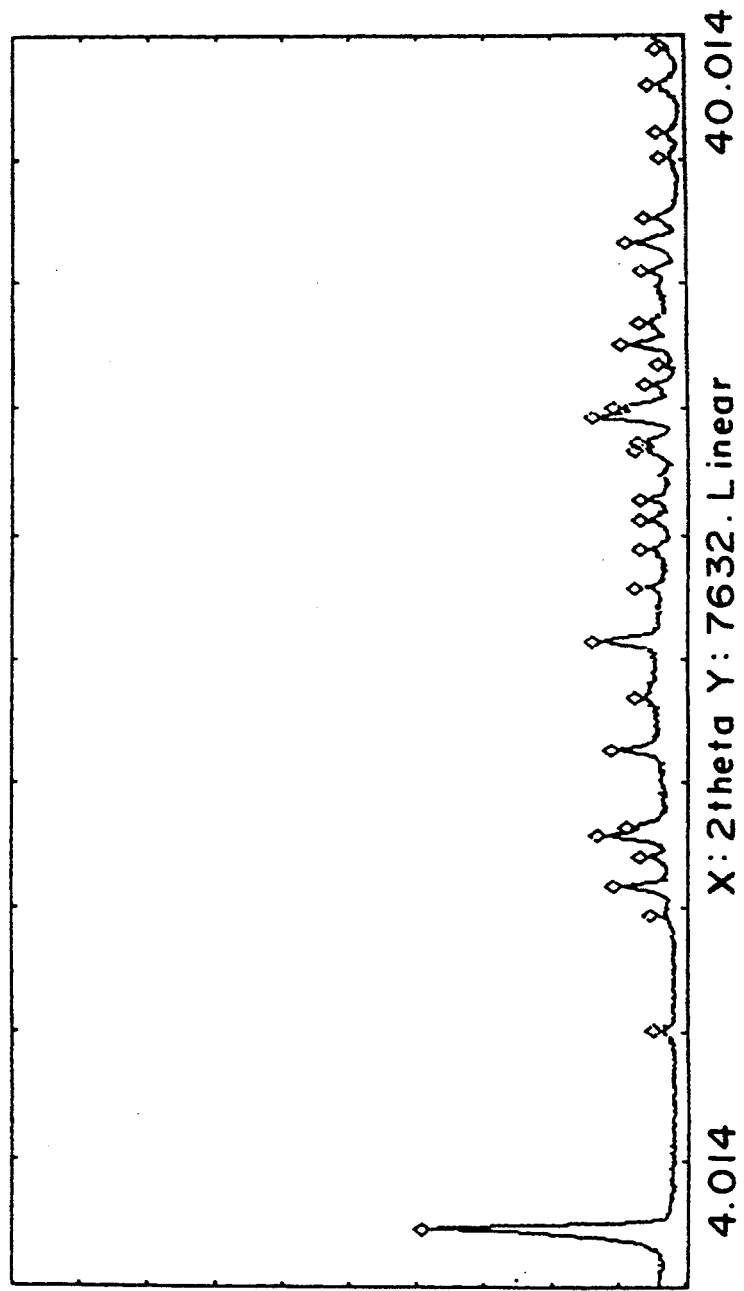

X-Ray Diffraction Spectrum: FIG. 10

The powder diagram is obtained under the same conditions as for form 1. The spectrum has a principal line at 5.6 and less intense lines at 29.0, 22.6 and 16.9, as indicated in Table 2 below.

TABLE 2

| 2theta | d | I rel. | 2theta | d | I rel. |
|---|---|---|---|---|---|
| 5.604 | 15.7570 | 100.0 | 5.604 | 15.7570 | 100.0 |
| 11.220 | 7.8797 | 9.6 | 29.015 | 3.0750 | 34.2 |
| 14.564 | 6.0772 | 10.2 | 22.572 | 3.9360 | 33.9 |
| 15.415 | 5.7435 | 25.2 | 16.876 | 5.2493 | 31.2 |
| 16.272 | 5.4430 | 14.7 | 19.386 | 4.5750 | 26.4 |
| 16.876 | 5.2493 | 31.2 | 29.274 | 3.0483 | 25.3 |
| 17.124 | 5.1740 | 20.5 | 15.415 | 5.7435 | 25.2 |
| 19.386 | 4.5750 | 26.4 | 31.085 | 2.8748 | 22.6 |
| 20.298 | 4.2413 | 17.3 | 17.124 | 5.1740 | 20.5 |
| 22.572 | 3.9360 | 33.9 | 34.088 | 2.6281 | 19.9 |
| 24.149 | 3.6825 | 17.2 | 20.928 | 4.2413 | 17.3 |
| 25.274 | 3.5209 | 14.5 | 24.149 | 3.6825 | 17.2 |
| 26.108 | 3.4103 | 14.9 | 28.035 | 3.1802 | 16.6 |
| 26.703 | 3.3358 | 14.9 | 28.286 | 3.1526 | 15.8 |
| 28.035 | 3.1802 | 16.6 | 31.733 | 2.8175 | 15.1 |
| 28.286 | 3.1526 | 15.8 | 26.703 | 3.3358 | 14.9 |
| 29.015 | 3.0750 | 34.2 | 26.108 | 3.4103 | 14.9 |
| 29.274 | 3.0483 | 25.3 | 16.272 | 5.4430 | 14.7 |
| 29.939 | 2.9821 | 12.5 | 25.274 | 3.5209 | 14.5 |
| 30.519 | 2.9267 | 7.4 | 33.226 | 2.6942 | 13.8 |
| 31.085 | 2.8748 | 22.6 | 29.939 | 2.9821 | 12.5 |
| 31.733 | 2.8175 | 15.1 | 34.809 | 2.5753 | 12.3 |
| 33.226 | 2.6942 | 13.8 | 38.661 | 2.3270 | 10.6 |
| 34.088 | 2.6281 | 19.9 | 14.564 | 6.0772 | 10.2 |
| 34.809 | 2.5753 | 12.3 | 11.220 | 7.8797 | 9.6 |
| 36.571 | 2.4551 | 6.8 | 37.278 | 2.4102 | 7.4 |
| 37.278 | 2.4102 | 7.4 | 30.519 | 2.9267 | 7.4 |
| 38.661 | 2.3270 | 10.6 | 39.654 | 2.2711 | 7.1 |
| 39.654 | 2.2711 | 7.1 | 36.571 | 2.4551 | 6.8 |

A comparison of the analytical results obtained with forms 1 and 2 shows that they are 2 different crystalline forms. In fact, although the elemental analysis shows the presence of one molecule of water in each of the forms, only form 2, obtained by the method according to the invention, is a monohydrate.

The following Examples describe other methods of preparing disodium tiludronate monohydrate. The product according to the invention obtained is characterized by the endothermic peak observed by differential calorimetric analysis (DCA). The conformity of the IR spectrum with that of Example 1 was verified for each of the products obtained.

EXAMPLE 2

100 g of tiludronic acid are suspended in 0.3 liter of water and the suspension is heated to 60° C. The pH of the medium is adjusted to between 4.6 and 4.8 by the addition of a 10% aqueous solution of sodium hydroxide. The pH is left to stabilize for 2 hours and the solution obtained is then filtered. The solution is heated to about 60° C. while 0.7 liter of acetone is added slowly, and reflux is maintained for 3 hours. The medium is left at room temperature and then cooled at 10° C. for 1 hour. The precipitate formed is filtered off and then dried in a ventilated oven at 60° C.

This gives 93 g of the salt in the expected crystalline form (form 2).

DCA: endothermic peak centred at 128° C.

EXAMPLES 3 TO 6

100 g of disodium tiludronate (form 1) are mixed with several volumes of water (nV), the mixture is heated to 70° C., several volumes of acetone (n'V) are then added and reflux is maintained for several hours. The mixture is left to return to room temperature and the precipitate formed is then filtered off and dried in a ventilated oven at 60° C.

The various Examples are collated in Table 3 below; the yield of disodium tiludronate (form 2) obtained has been indicated for each Example.

TABLE 3

| Example no. | Water nV (1) | Acetone n'V (1) | Total V (1) | Yield | DCA °C. |
|---|---|---|---|---|---|
| 3 | 0.3 | 0.2 | 0.5 | 93 g | 129 |
| 4 | 0.4 | 0.4 | 0.8 | 87 g | 122 |
| 5 | 0.4 | 0.7 | 1.1 | 85 g | 122 |
| 6 | 0.3 | 0.7 | 1.0 | 85 g | 120 |

EXAMPLES 7 AND 8

100 g of disodium tiludronate (form 1) are mixed with 0.4 liter of water, with stirring, and the mixture is heated to 90° C. After 1 hour, the solution is clarified by filtration and 0.7 liter of acetone is then poured into the solution, the temperature being allowed to drop to about 60° C. After 1 hour at 60° C., the mixture is left to return to room temperature and the precipitate present is then filtered off; the resulting moist precipitate is taken up in 1 liter of a solvent which permits azeotropic distillation under atmospheric pressure.

The solvents used are either ethyl acetate or isopropyl ether, which enable the salt to be obtained in the expected crystalline form (form 2) with the following yields: 89% and 97%; DCA: endothermic peak centred at 118° C.

EXAMPLES 9 TO 13

0.2 liter of water is heated to 80° C. and 100 g of disodium tiludronate (form 1) are added over 1 hour. After 5 hours at 80° C., the temperature is lowered by 5° C. per hour to 20° C. and the precipitate formed is filtered off. This precipitate is divided up into several portions, which are dried by different means to give the salt in the expected crystalline form (form 2).

Drying at 60° C. in a ventilated oven, yield: 75%
Azeotropic distillation
  with 3-methylbutanone, yield: 91%
  with n-butanol, yield: 89%
  with dichloroethane, yield: 93%; DCA: endothermic peak centred at 113° C.
  with toluene, yield: 97%; DCA: endothermic peak centred at 117° C.

EXAMPLE 14

100 g of disodium tiludronate (form 1) are ground and the powder is spread out in a crystallizing dish of diameter 23 cm to a height of 0.5 cm. The crystallizing dish is placed in a desiccator containing water in the bottom part. The desiccator is closed and placed in an oven at 65°–70° C. for 3 days. The powder contained in the crystallizing dish is then dried for one day in a ventilated oven at 50° C.

This gives 100 g of the salt in the expected crystalline form (form 2). The structure is confirmed by the analytical results: the IR, TGA and X-ray diffraction spectra conform to those obtained in Example 1.

EXAMPLE 15

The stability of disodium tiludronate monohydrate with time was studied as a function of the variable temperature and humidity conditions.

No degradation product was evident after storage for 6 months under normal temperature and humidity conditions, showing the good chemical stability of the monohydrate. The physical stability of this crystalline form was studied under the conditions explained below.

A saturated salt solution is placed in the bottom of a hermetically sealed vessel, making it possible to obtain the desired relative humidity at different temperatures. 500 mg of form 2 to be studied are placed on a support arranged above the saturated salt solution. After several days (d) at a defined temperature (T° C.) and in a defined relative humidity (RH), the weight increase (ΔM %) is measured and Karl-Fischer analysis is used to verify that the weight increase is due to the increase in the water content.

The results obtained are given in Table 4 below.

TABLE 4

| | (Form 2) | | | | | | |
|---|---|---|---|---|---|---|---|
| | RH % | | | | | | |
| T° C., time | 33 | 43 | 53 | 58 | 75 | 85 | |
| 50° C., 49 days | 0 | 0 | 0 | 0 | 0 | 0.3 | ΔM % |
| | (2) | (2) | (2) | (2) | (2) | (2) | Identification |
| 35° C., 41 days | 0 | 0 | 0 | 0 | 0 | 0 | ΔM % |
| | (2) | (2) | (2) | (2) | (2) | (2) | Identification |
| 25° C., 58 days | 0 | 0 | 0.5 | 0.55 | 0.9 | 1.4 | ΔM % |
| | (2) | (2) | (2) | (2) | (2) | (2) | Identification |

The results show that form 2, i.e. disodium tiludronate monohydrate, is stable. The only variation observed is a slight weight increase (about 1%) at 25° C., in a relative humidity above 75% and after 58 days.

EXAMPLE 16

A tablet having the following composition is prepared by dry granulation:

| | |
|---|---|
| disodium tiludronate monohydrate: | 240 mg |
| sodium laurylsulfate: | 4.5 mg |
| anhydrous colloidal silica: | 1.3 mg |
| microcrystalline cellulose: | 21.6 mg |
| crosslinked polyvinylpyrrolidone: | 8.0 mg |
| magnesium stearate: | 5.6 mg |
| anhydrous lactose for a finished tablet of: | 320 mg |

EXAMPLE 17

A tablet having the following composition is prepared by wet granulation:

| | |
|---|---|
| disodium tiludronate monohydrate: | 240 mg |
| sodium laurylsulfate: | 4.5 mg |
| methyl hydroxypropyl cellulose: | 5.25 mg |
| crosslinked polyvinylpyrrolidone: | 15.0 mg |
| magnesium stearate: | 0.60 mg |
| purified water: | |
| lactose for a finished tablet of: | 300 mg |

The tablets of Examples 17 and 18 were stored for 15 months at room temperature. After this storage time, the results of the analytical studies performed on the powdered tablets indicate that disodium tiludronate (form 2) is stable in the pharmaceutical form.

The IR and TGA spectra of the tablets of Examples 17 and 18 conform to those obtained in Example 1.

What is claimed is:

1. Disodium tiludronate monohydrate.

2. The disodium tiludronate monohydrate of claim 1 which has an IR spectrum run at 4% (m/v) in potassium bromide, comprising the following bands: 3600, 3400, 2920, 1600, 1480, 1390, 1300, 1090, 1050, 900, 820 and 710 cm$^{-1}$.

3. The disodium tiludronate monohydrate of claim 1 which has an X-ray diffraction spectrum measured on the crystalline powder, comprising a principal line for a value of $2\theta$ of 5.60 and lines at 29.0, 22.6 and 16.9.

4. The disodium tiludronate monohydrate of claim 1 which has a DCA spectrum which has an endothermic peak at 121°±8° C.

5. The disodium tiludronate monohydrate of claim 1 which has a weight loss curve on thermogravimetric analysis shown in FIG. 8.

6. Disodium tiludronate monohydrate characterized by:
   its IR spectrum run at 1% (m/v) in potassium bromide, comprising the following bands: 3600, 3400, 2920, 1600, 1480, 1390, 1300, 1090, 1050, 900, 820, 710 cm$^{-1}$;
   its X-ray diffraction spectrum measured on the crystalline powder, comprising a principal line for a value of $2\theta$ of 5.60 and lines at 29.0, 22.6 and 16.9;
   its DCA spectrum, which has an endothermic peak at 121°±8° C.;
   its weight loss curve on thermogravimetric analysis, shown in FIG. 8.

7. A pharmaceutical composition comprising an effective amount of disodium tiludronate monohydrate and a pharmaceutically acceptable agent or excipient.

8. A pharmaceutical composition according to claim 7 in a form suitable for oral administration.

9. A pharmaceutical composition according to claim 8 in tablet form.

10. A pharmaceutical composition according to claim 8 in effervescent oral form.

11. A pharmaceutical composition according to claim 10 which further comprises an effervescent couple.

12. A pharmaceutical composition according to claim 11 wherein the effervescent couple is tartaric acid and sodium bicarbonate, or citric acid and sodium bicarbonate.

* * * * *